United States Patent [19]
Bogaert

[11] 4,364,473
[45] Dec. 21, 1982

[54] OUTFIT FOR REPAIR OF SPLIT DENTAL PROSTHESIS

[75] Inventor: Jean-Pierre Bogaert, Brussels, Belgium

[73] Assignee: Bonyf AG, Schaan, Liechtenstein

[21] Appl. No.: 222,745

[22] Filed: Jan. 5, 1981

Related U.S. Application Data

[62] Division of Ser. No. 82,897, Oct. 3, 1979, Pat. No. 4,270,904.

[51] Int. Cl.³ .............................................. B65D 85/32
[52] U.S. Cl. .................................. 206/63.5; 206/568; 206/582
[58] Field of Search .................. 206/568, 582, 63.5, 206/45.19

[56] References Cited

U.S. PATENT DOCUMENTS

| | | | |
|---|---|---|---|
| 2,874,832 | 2/1959 | Gordon | 206/63.5 |
| 3,336,669 | 8/1967 | Kramer | 206/63.5 |
| 3,346,147 | 10/1967 | Higgins et al. | 206/63.5 |
| 4,294,349 | 10/1981 | Ibsen et al. | 206/568 |

*Primary Examiner*—William T. Dixson, Jr.
*Attorney, Agent, or Firm*—Flehr, Hohbach, Test, Albritton & Herbert

[57] ABSTRACT

An outfit for repairing a split or broken dental prosthesis including a package, a tube of non-toxic fast-setting adhesive, container means for separately containing a monomer and polymer which when mixed together form a resin, and a support which is contained by the package for receiving and separately supporting the container means for the monomer and polymer and the tube of adhesive.

4 Claims, 4 Drawing Figures

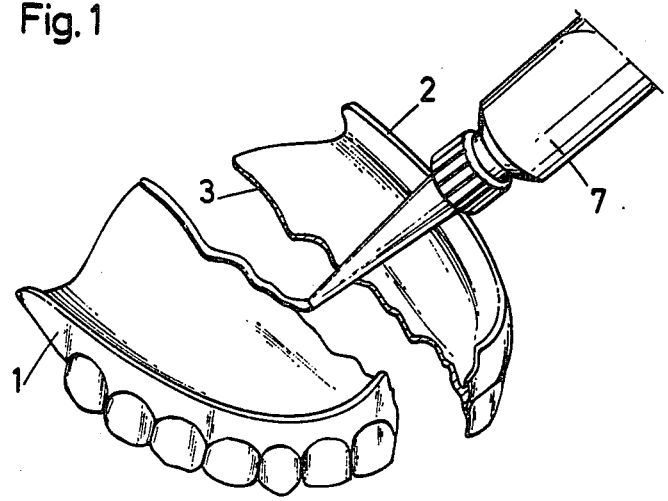
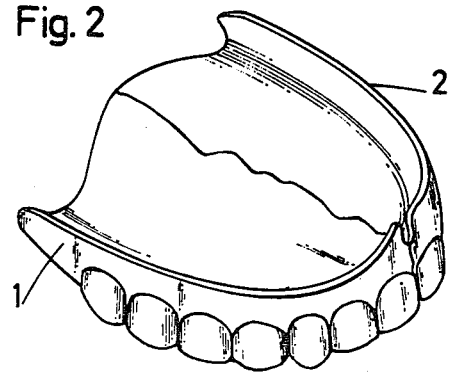
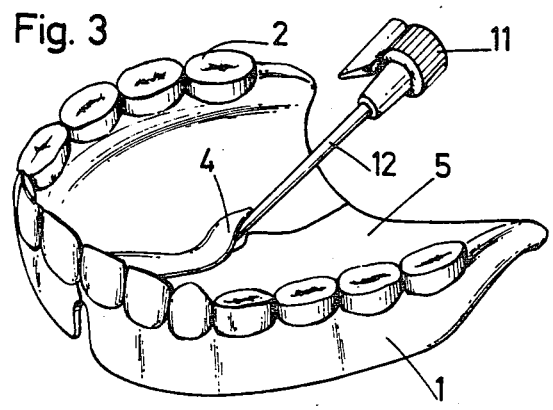

OUTFIT FOR REPAIR OF SPLIT DENTAL PROSTHESIS

This is a division of application, Ser. No. 82,897, filed Oct. 3, 1979, and now U.S. Pat. No. 4,270,904.

This invention relates to an outfit for repairing a split or broken dental prosthesis.

When it is presently required to repair a dental prosthesis which has for instance been broken into two parts, both said parts are first assembled in the initial relative position thereof inside a plaster mold which has been specificaly cast for this particular prosthesis. There is then removed a wide enough material strip from the prosthesis where same has been broken and into the gap thus formed is poured liquid resin to join together again both prosthesis parts. The surfaces adjacent the break are finally smoothed.

Such a repair takes a relatively long time and due to the required accuracy, special tooling is required in such a way that the repair can only be made by the man of the art.

One of the main objects of the invention is to obviate this drawback and to provide an extremely simple method allowing that very individual the broken prosthesis belongs to, to perform directly the repair of the prothesis and in such a way as to obtain a fastening which is at least as strong as the one obtained with the conventional method as outlined above.

For this purpose with the method according to the invention, the corresponding break surfaces of the prosthesis are fastened to one another by means of a non-toxic fast-setting adhesive, having an affinity for the material the prosthesis is made of, and thereafter on the lingual surface of said prosthesis facing said break surfaces fastened together, there is formed a butt-strip from polyacrylic resin having some width, said strip being fastened to the lingual surface on either side of said break surfaces.

The invention also pertains to a dental prosthesis which has been repaired according to said method, as well as to a specific outfit for the working of said method.

Said outfit comprises a package which contains on the one hand, a tube from non-toxic fast-setting adhesive having an affinity for the material the prosthesis is made of, and on the other hand, acrylic acid-based monomer and powdered polymer on the basis of polyvinyl acetate, said monomer and polymer being kept separated from one another.

Other details and features from the invention will stand out from the following description given by way of non limitative example and with reference to the accompanying drawings, in which:

FIGS. 1 to 3 show various stages of a preferred embodiment of the method according to the invention.

In the various figures, the same reference numerals pertain to similar elements.

FIGS. 1 to 3 show the repairing of a dental prosthesis which has been broken into two parts 1 and 2.

Figure 4:
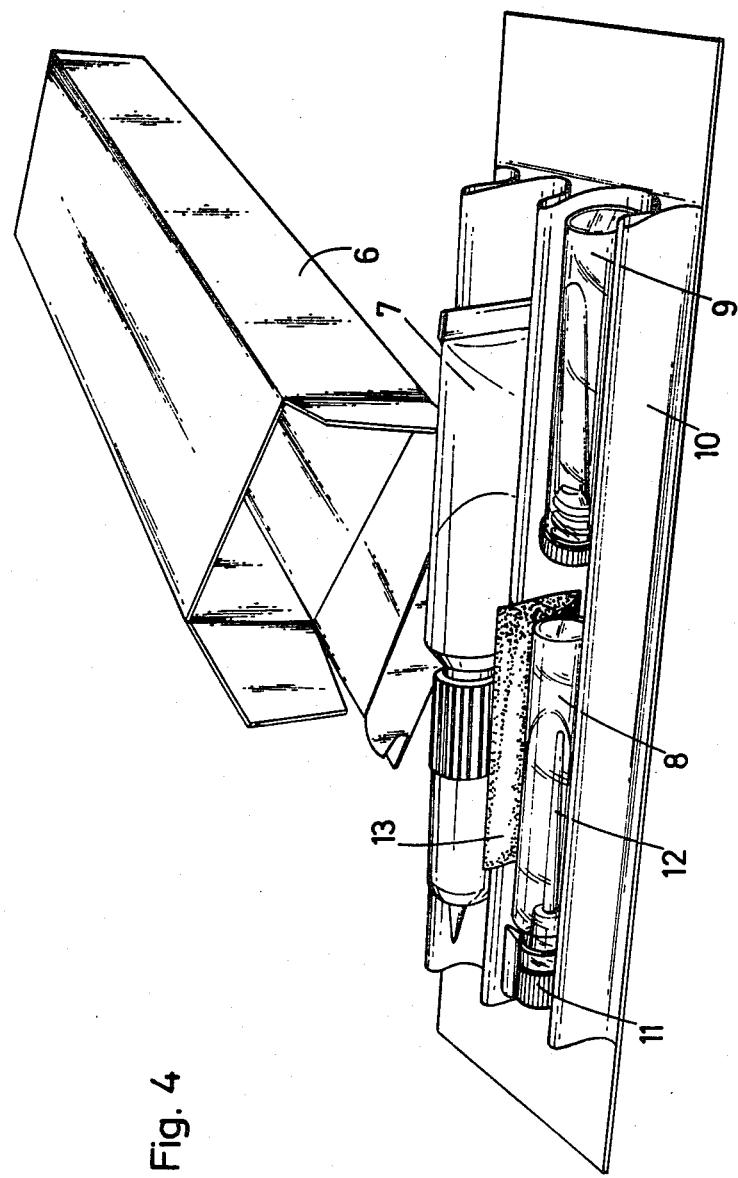
FIG. 4 is perspective view from a specific outfit according to the invention.

The preliminary operations comprise thoroughly cleaning both parts where the break lies and drying at least the break surface 3 from each part.

Then as shown in FIG. 1, to the break surface of the one part 1 is applied a layer from non-toxic fast-setting adhesive having an affinity for that material the prosthesis is made of and both parts are assembled in the original relative position thereof by joining the corresponding break surfaces together by means of said adhesive as shown in FIG. 2.

The adhesive used is advantageously an adhesive on the basis of alkyl-α-cyanoacrylate, such as the one known under the registered trade-mark "Three-Bond".

In the following stage there is formed facing said break surfaces joined together, a butt-strip 4 from polyacrylic resin with a width in the range from 0.5 to 1 cm and a thickness in the range from 1 to 2 mm which fastens to the lingual surface 5 of the prosthesis, that is, the smooth surface opposite that surface which is to be applied against the mouth roof.

To insure a good fastening of the butt-stripp, that lingual surface portion on which the butt-strip is to be applied is first rubbed-down with emery-paper.

The butt-strip is formed by first mixing substantially equal-weight portions from a powdered polymer on the basis of polyvinyl acetate and a liquid monomer on the basis of methacrylic acid, during 1 minute at the most, until a substantially homogeneous putty is obtained. Said putty is then directly applied to the prosthesis lingual surface where it hardens fast by copolymerizing of the polyvinyl acetate and methacrylic acid to be joined closely to the prosthesis.

After hardening, the butt-strip thus formed is rubbed lightly with liquid monomer to smoothen same.

Comparative tests have been made with a break repaired according to the above-described conventional method and a break repaired according to the method according to the invention, and it has been noticed that the method according to the invention imparts to the prosthesis a higher resistance to those stresses the prosthesis is normally subjected to than said conventional method, due among other factors to the reinforced area formed at the location of the break by the butt-strip in addition to the fastening by the adhesive.

To make working the method according to the invention even easier, a specific outfit is proposed. Said outfit, a specific embodiment of which is shown in FIG. 4, comprises a package 6 containing on the one hand, a tube from said adhesive 7 and on the other hand, monomer and polymer separated from one another by keeping same for instance each in a bottle 8, 9. Said bottles are calibrated to make it easier to proportion the monomer and polymer when preparing the putty. Moreover the cover 11 of the one bottle, for instance bottle 8, is provided with a rod 12 to mix the monomer and polymer. Both bottles and the tube are received in a suitable support 10 which is slipped into the package.

Said outfit may finally be completed with a piece of emery-paper 13.

The contents of the tube and bottles may for example correspond to one or two repairs of a dental prothesis.

It must be understood that the invention is in no way limited to the above embodiments and that many changes can be brought therein without departing from the scope of the invention as defined by the appended claims.

For instance the two discrete bottles may advantageously be replaced by a single bottle with two chambers separated by a punchable or removable wall and for example in the shape of a syringe.

Moreover both the adhesive and the resin used can be of another type as long as they are consistent with the material of the dental prosthesis.

I claim:

1. An outfit for repairing a split or broken dental prosthesis comprising: a package; a tube of non toxic fast-setting adhesive having an affinity for the material the prosthesis is made of; container means for separately containing a monomer and polymer which when mixed together form a resin; and a support which is contained by said package said support including means for receiving and separately supporting said container means and said tube of adhesive.

2. An outfit as in claim 1, in which the polymer and monomer are each contained in a calibrated bottle.

3. An outfit as in claim 1, in which one said bottle has a cover provided with a rod for the mixing of said monomer and polymer.

4. An outfit as in claim 1 where said resin is polyacrylic, said monomer is acrylic acid-based, and said polymer is on the basis of polyvinyl acetate.

* * * * *